United States Patent [19]

Ishizaki et al.

[11] 4,378,810
[45] Apr. 5, 1983

[54] ASSEMBLY FOR PERFORMING BIOPSIES USING A COMBINATION PROBE-GUIDE

[75] Inventors: Goro Ishizaki; Harold R. Parker, both of Davis, Calif.

[73] Assignee: The Regents of the University of California, Berkeley, Calif.

[21] Appl. No.: 247,791

[22] Filed: Mar. 26, 1981

[51] Int. Cl.³ .......................................... A61B 10/00
[52] U.S. Cl. ................................. 128/754; 128/305
[58] Field of Search ..................... 128/305, 305.1, 310, 128/321, 214.4, 754

[56] References Cited

U.S. PATENT DOCUMENTS

| | | | |
|---|---|---|---|
| 2,850,007 | 9/1958 | Lingley | 128/305 |
| 3,515,137 | 6/1970 | Santomieri | 128/214.4 |
| 3,545,443 | 12/1970 | Ansari | 128/214.4 |
| 3,572,334 | 3/1971 | Petterson | 128/214.4 |
| 3,584,625 | 6/1971 | Swick | 128/214.4 |
| 3,595,217 | 7/1971 | Rheinfrank | 128/214.4 |
| 3,844,272 | 10/1974 | Banko | 128/305 |
| 4,142,517 | 3/1979 | Stavropoulos et al. | 128/310 |
| 4,256,119 | 3/1981 | Gauthier | 128/347 |

*Primary Examiner*—Kyle L. Howell
*Assistant Examiner*—Daniel P. Burke
*Attorney, Agent, or Firm*—Flehr, Hohbach, Test, Albritton & Herbert

[57] ABSTRACT

An assembly especially suitable for performing biopsies on living organs or tissue is disclosed herein. The assembly includes a specifically designed open-ended hollow tubular member serving as a combination probe and guide, a specifically designed handle for holding the tubular member during performance of the biopsy and means including a needle positionable through the tubular member for collecting a specimen from the tissue. The assembly may also include means for controlling the depth of penetration of the needle into the tissue, means for preventing the tissue collected by the needle from passing entirely through the latter and a stylet serving both to protect the needle and as a means for applying local anesthetic to the organ or tissue to be biopsied.

8 Claims, 16 Drawing Figures

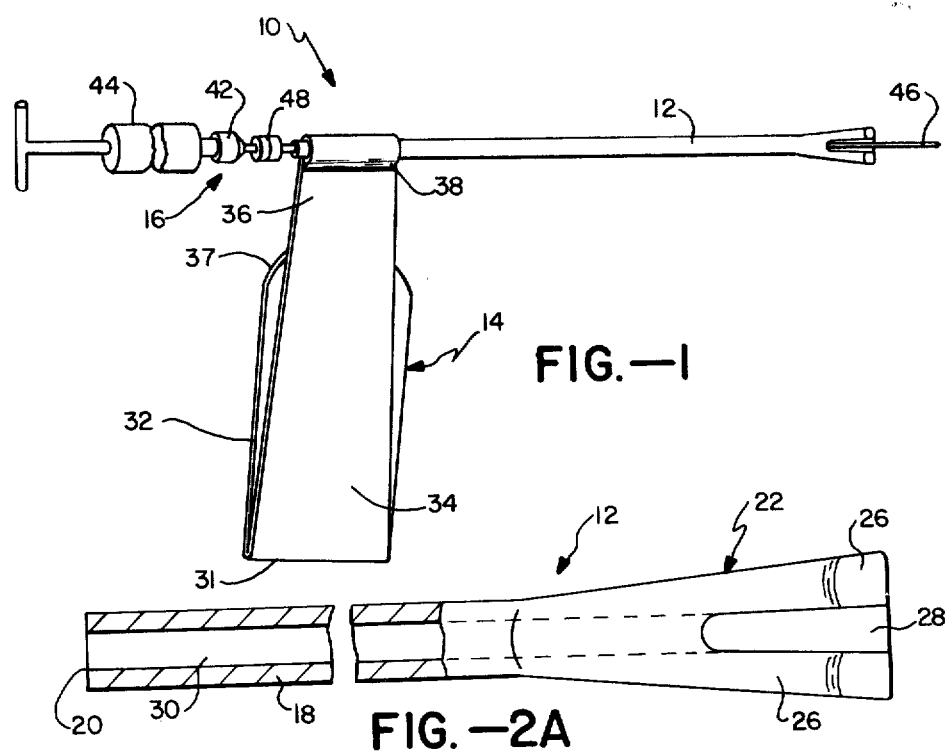
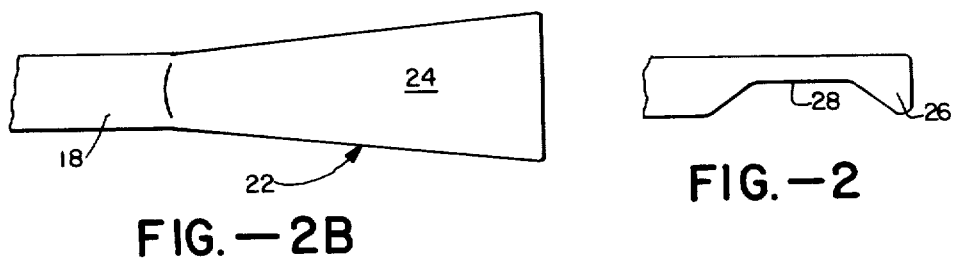
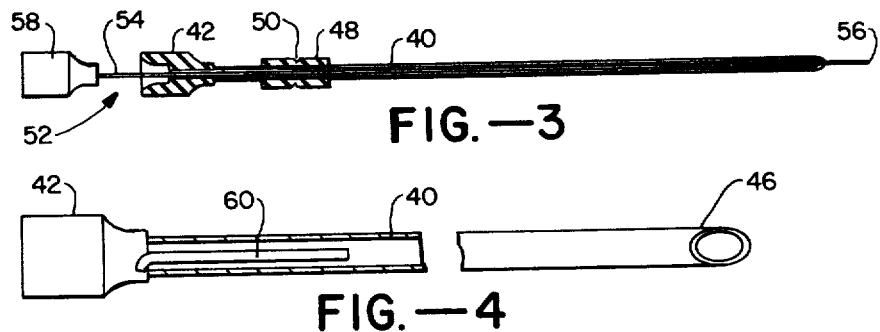

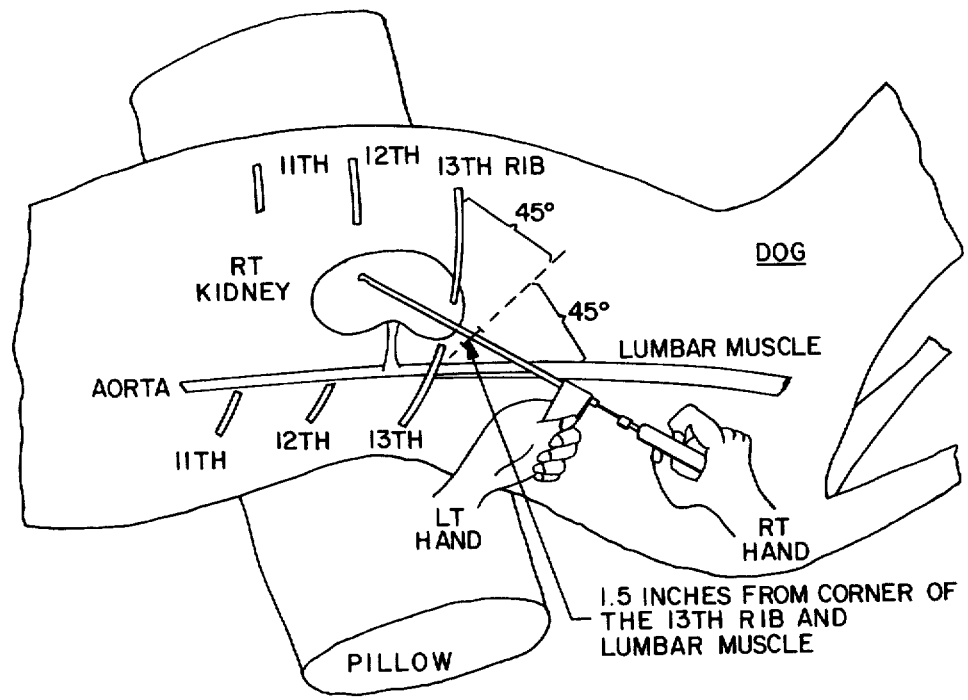
FIG.—5A
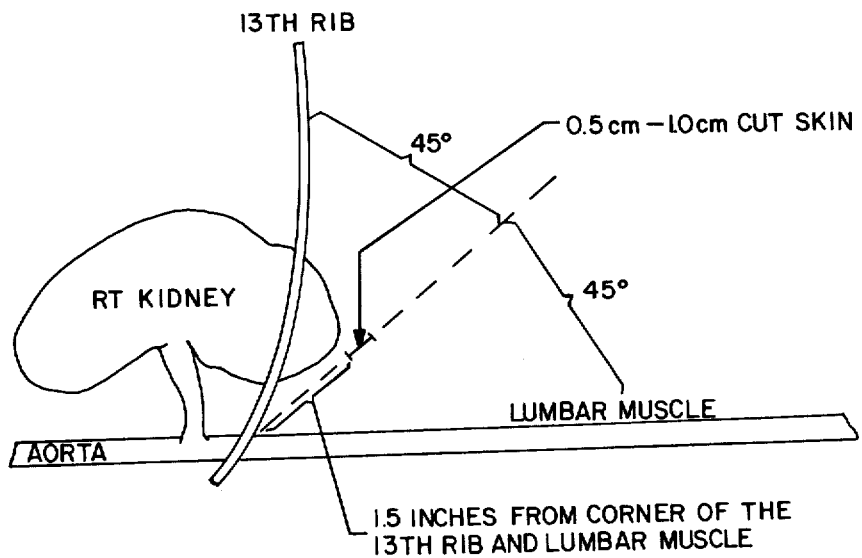
FIG.—5B

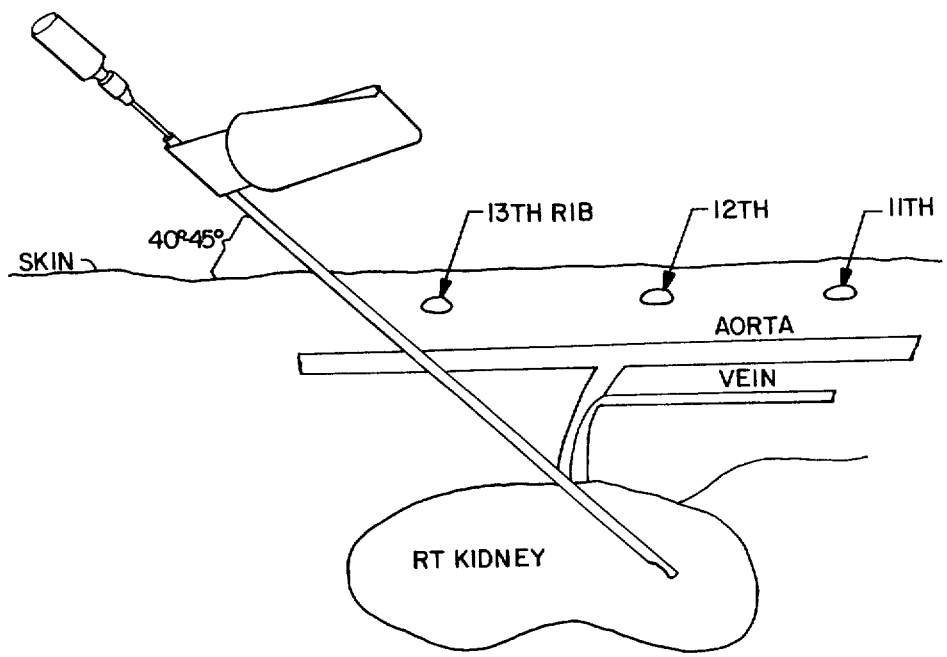
FIG.—6A
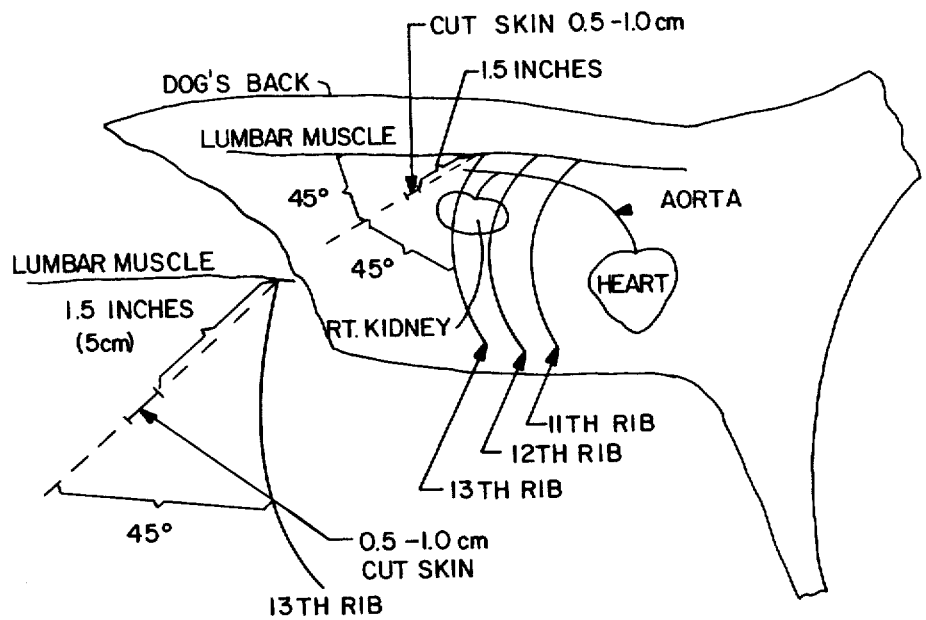
FIG.—6B

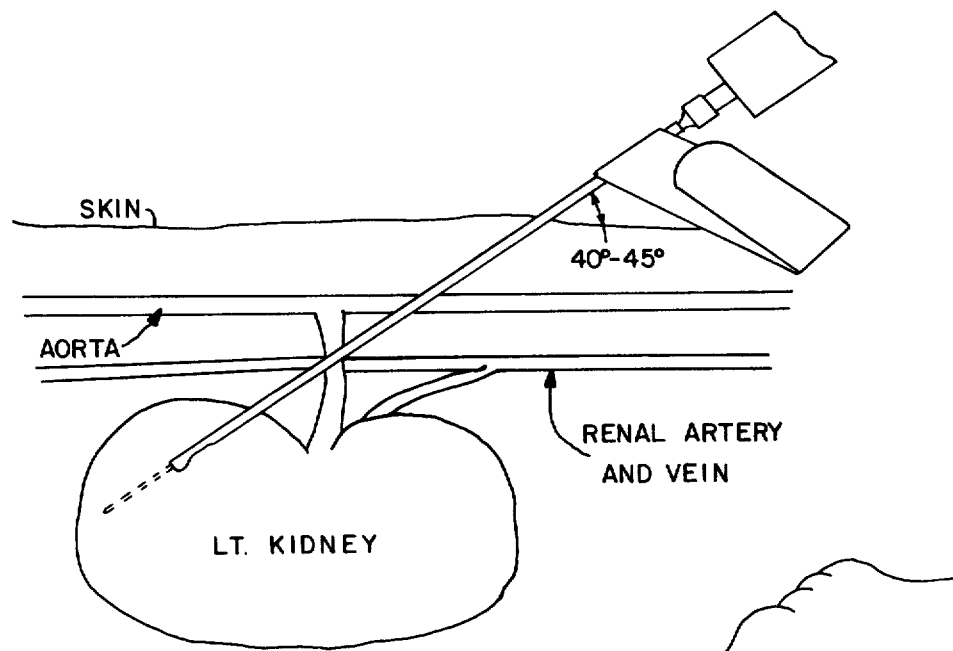
FIG.—7A
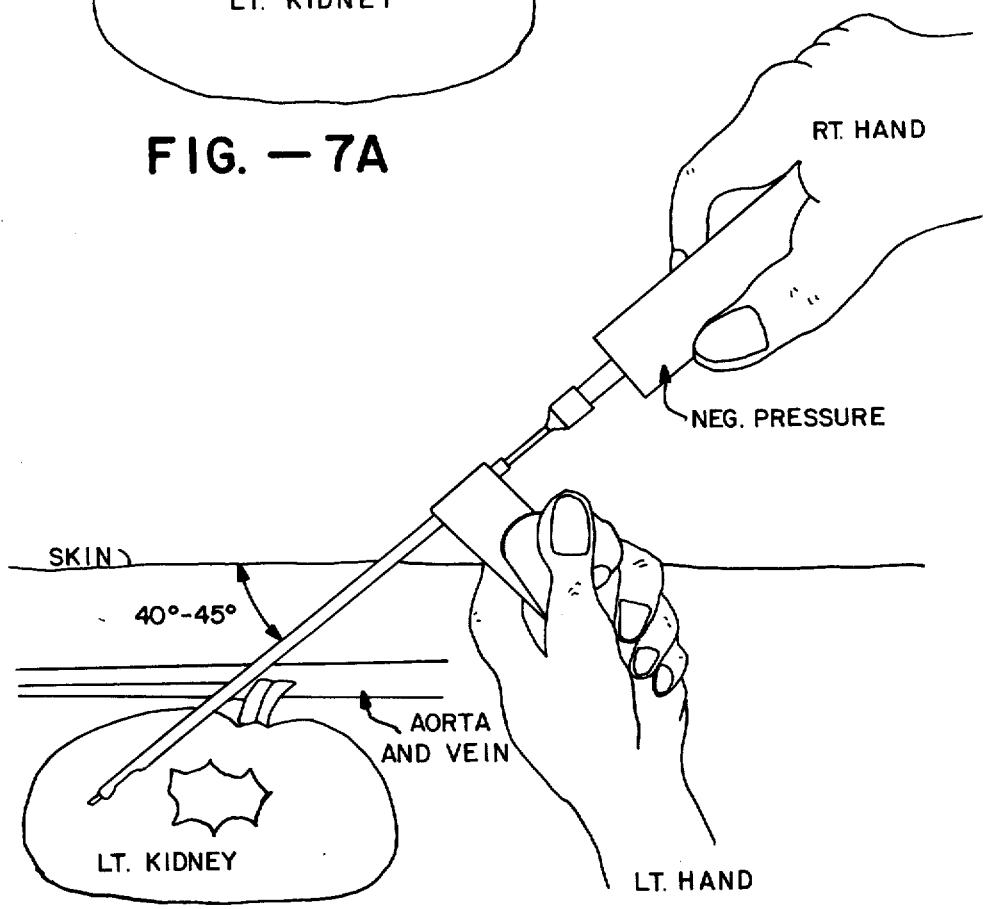
FIG.—7B

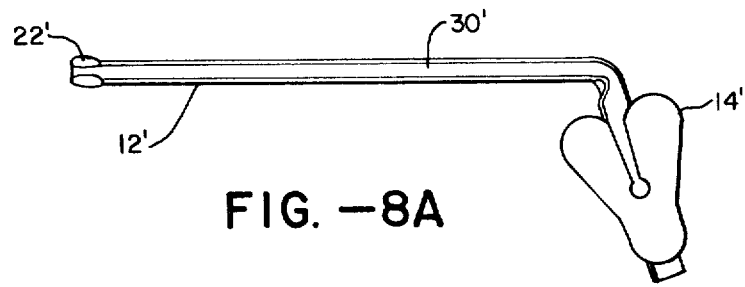
FIG.—8A
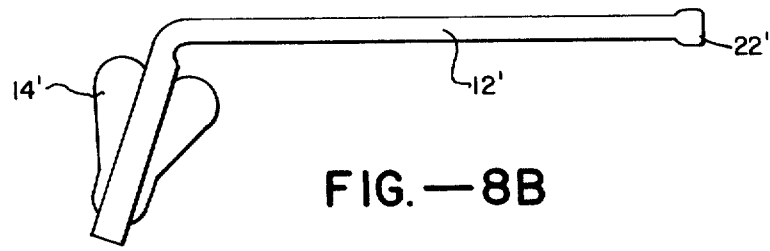
FIG.—8B
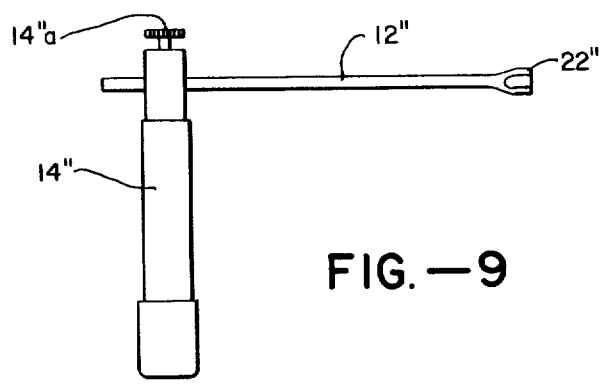
FIG.—9
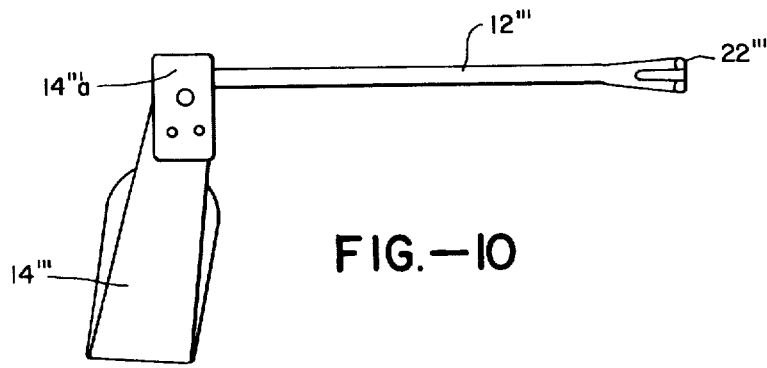
FIG.—10

ASSEMBLY FOR PERFORMING BIOPSIES USING A COMBINATION PROBE-GUIDE

The present invention relates generally to the performance of biopsies on living tissue in animals or humans and more particularly to a specific assembly for performing such biopsies, especially on kidneys and other internal organs. In this regard, the term "biopsy" refers to a procedure for collecting a piece of living tissue and may be carried out in accordance with many different techniques, as exemplified in the following publications:

Kark, Robert M.: Renal Biopsy. JAMA 205:80–86, 1968.

Iversen, Poul and Brun, Claus: Aspiration Biopsy of the Kidney. American Journal of Medicine, September 1951, pp. 324–330.

Osborne, Carl A.: Clinical Evaluation of Needle Biopsy of the Kidney and Its Complications in the Dog and Cat. J.A.V.M.A. 158:1213–1228, 1971.

Osborne, Carl A., Delmar, Finco R., Low, Donald G., Perman, Victor: Percutaneous Renal Biopsy in the Dog and Cat. J.A.V.M.A. 151:1474–1480, 1967.

Kerr, David N. S.: Renal Biopsy with Modified Menghini Needle. The Lancet, December 1960, pp. 1370–1373.

In: DIAGNOSIS OF URNIARY DISEASES. Chapter 9, Percutaneous Renal Biopsy. pp. 107–117.

Osborne, Carl A.: Modified Franklin-Silverman Biopsy Needle. Journal of Urology 107:358–359, 1972.

Lavastida, Marta T., Musil, Geroge, Hulet, William H.: A Disposable Needle for Percutaneous Renal Biopsy. Clinical Pediatrics 3:170–173, 1968.

Osborne, Carl A. and Low, Donald G.: Size, Adequacy, and Artifacts of Canine Renal Biopsy Samples. Am. J. Vet. Res. 32:1865–1871, 1971.

DeBeukelaer, Martin M., Schreiber, Melvyn H., Dodge, Warren F. and Travis, Luther B.: Intrarenal arteriovenous fistulas following needle biopsy of the kidney. Journal of PEDIATRICS 78:266–272, 1971.

While the various publications listed above describe a number of different techniques for performing biopsies, especially kidney biopsies on animals, utilizing various types of instruments, it is the primary object of the present invention to provide an improved instrument or actually assembly of components especially suitable for performing kidney, liver and like biopsies on animals and humans.

A more particular object of the present invention is to provide an assembly for performing biopsies in a safe, reliable manner.

Another particular object of the present invention is to provide an assembly for performing a kidney, liver or like internal biopsy in a way which requires only a slight outer entry incision to the patient whereby to reduce the possibility of trauma.

Still another particular object of the present invention is to provide an assembly of the last-mentioned type which is capable of collecting a relatively large biopsy specimen even though the entry incision may be quite small.

Yet another particular object of the present invention is to provide an assembly of the last-mentioned type and specifically one which utilizes a needle for collecting the biopsy specimen and means for accurately controlling the position of the needle including its depth of penetration as the needle is guided into the tissue being biopsied, whereby to minimize permanent damage to the latter.

Still another particular object of the present invention is to provide an assembly for performing kidney, liver and like biopsies and specifically an assembly which is capable of determining the size and consistency of as well as certain irregularities in the tissue being biopsied without having to enlarge the entry incision over and above that which is necessary to perform the biopsy itself.

Still another particular object of the present invention is to provide an assembly of the last-mentioned type and specifically one which utilizes a needle and means serving to protect the needle and also as an applicator for applying local anesthetic to the tissue being biopsied.

A further object of the present invention is to provide various methods of carrying out a kidney, liver or like biopsy on an animal or human utilizing the specific assembly of components disclosed herein.

As will be seen hereinafter, the assembly disclosed herein includes an elongated member which serves as a combination probe and guide (hereinafter referred to as a probe-guide) having a front end section and a back end section. The assembly also includes a spring steel handle connected with the probe-guide for controlling tension applied to the organ or tissue as well as to position the latter as the biopsy is carried out and means including a needle which is carried by the combination probe-guide and which serves to actually collect the biopsy specimen.

In accordance with one aspect of the present invention, the combination probe-guide just recited is designed as an open-ended hollow tubular member including a front end section having on one side thereof a substantially flat and smooth exterior surface and spaced finger-like segments on an opposite side. The flat exterior surface is provided for palpating the organ or tissue being biopsied whereby to determine the size, shape and consistency of the organ or tissue in question and to identify any bumps or other such irregularities. The finger-like segments serve to hold the organ or tissue in an immobile position while a biopsy specimen is collected by the needle. As a result of these features, the doctor does not have to use a finger to initially examine the organ or tissue being biopsied or to immobilize the organ or tissue during the biopsies as was often done previously. Therefore, it is not necessary to provide a large enough entry incision or a second incision to accommodate the doctor's finger. Moreover, the open-ended tubular design of the combination probe-guide together with its finger-like segments serve as a reliable guide for accurate placement of the specimen collecting needle and particularly its forwardmost point.

Another aspect of the present invention resides in the utilization of a specifically designed handle which not only serves as a means for controlling the position of the combination probe-guide but also as means for causing the front end section of the latter to bear against the tissue being biopsied in a controlled manner. This latter feature is accomplished by designing the handle so that the individual holding it can accurately sense the amount of force exerted by the probe-guide on the organ or tissue. In a preferred embodiment, the handle is constructed of spring steel sheet material connected directly to the back end section of the combination probe-guide and folded back on itself in a direction transverse to the latter.

Still another aspect of the present invention resides in the utilization of a self-retaining tubular spacer which is positioned around the needle itself without damaging the latter. In this way, as the needle is guided through the combination probe-guide, the spacer limits the extent to which the needle passes through it. This, in turn, controls the depth of penetration of the needle into the tissue being biopsied, thereby minimizing damage to the latter and therefore making it possible to perform a number of biopsies on the same organ or tissue.

Other aspects of the present invention include the utilization of a hollow stylet having a blunt tip at its front end. This stylet serves as an insert into the needle to protect its pointed end and, apart from the needle, it serves to spray a local anesthetic onto the organ or tissue being biopsied.

Still other aspects of the present invention will become apparent from the following detailed description in conjunction with the drawings wherein:

FIG. 1 is a perspective view of an assembly which is designed in accordance with the present invention to perform biopsies on living tissue, especially kidney organs in animals;

FIG. 2A is a partially broken away lengthwise view of one side of a combination probe-guide forming part of the overall assembly of FIG. 1;

FIG. 2B is lengthwise view of a portion of the combination probe-guide of FIG. 2A but shown from the opposite side;

FIG. 2C is a lengthwise view of a portion of the combination probe-guide of FIG. 2A but shown along one side edge;

FIG. 3 is a lengthwise sectional view of a needle arrangement comprising part of the overall assembly illustrated in FIG. 1;

FIG. 4 is an enlarged lengthwise sectional view of an end portion of a needle forming part of the arrangement of FIG. 3 and including a tissue stop also forming part of the arrangement;

FIGS. 5A, 5B, 6A, 6B and 7A, 7B are diagrammatic illustrations of the way in which the assembly of FIG. 1 is used to obtain a biopsy specimen from the kidney of a dog; and FIGS. 8A, 8B, 9 and 10 are side elevational views illustrating modified probe-guides and/or handles for the latter.

Turning now to the drawings, wherein like components are designated by like reference numerals throughout the various figures, attention is first directed to FIG. 1 which illustrates an assembly 10 designed in accordance with the present invention to perform biopsies on living tissue, especially the kidney organ of an animal. As seen in FIG. 1, this assembly includes a combination probe-guide 12, a handle 14 and a needle arrangement 16. As will be seen hereinafter, the combination probe-guide is essentially an open-ended hollow tubular member which is held at its rearwardmost end by handle 14 and which is adapted to receive a needle forming part of arrangement 16 through its back end. The probe-guide itself serves to palpate the kidney or other organ or tissue being examined for size, shape, consistency and irregularities generally such as bumps or swellings. It may also be utilized to hold the kidney or other organ or tissue in place as the biopsy is performed and as a guide for the needle during this process. In this regard, handle 14 serves to manipulate the combination probe-guide during both procedures, that is, during the preliminary search and evaluation procedure and during the subsequent biopsy.

Needle arrangement 16 not only provides the needle necessary to perform the biopsy but also serves several other purposes to be discussed hereinafter.

Turning to FIGS. 2A and 2B, attention is directed specifically to the combination probe-guide 12. As stated above, this component is in the form of an open-ended tubular member which, as seen in FIG. 2A, includes a straight tubular body 18 having an opened back end 20 and an enlarged front end section 22. As seen in FIG. 2B, one side of front end section 22 includes a flat exterior surface 24 which serves to palpate the surface of the organ or tissue being biopsied for the reasons discussed above. The opposite side of front end section 22 includes finger-like segments 26 which extend in the same direction as tubular body 18 and which are spaced from one another by an elongated opening 28 therebetween. FIG. 2C shows the finger-like members which serve to immobilize the organ or tissue being biopsied as the biopsy specimen is collected. In this regard, opening 28 opens into the longitudinal passageway through tubular body 18, which passageway is generally indicated at 30. As a result, the finger-like segments 26 can be maintained tightly against the organ or tissue being biopsied while the combination of opening 28 and passageway 30 serve to guide a needle to the target point between the finger-like segments for collecting a biopsy specimen. In an actual working embodiment, the finger-like segments are themselves smoothly rounded (see FIG. 2C), preferably in parallel relationship with flat surface 24 and the overall combination probe-guide is constructed of 18-8 stainless steel in this actual embodiment.

Having described the combination probe-guide 12, attention is now directed to handle 14 which is illustrated only in FIG. 1. As seen there, the handle is actually an elongated, sheet-like member which is folded back on itself at 31 to provide two layers 32 and 34. Layer 34 includes an end section 36 which extends beyond the free end 37 of layer 32 and which wraps around a rearward end section of tubular body 18 at 38. Section 38 of the handle is fixedly connected in place to body 18 by any suitable means so as to extend normal thereto, as seen in FIG. 1. In an actual working embodiment, a silver soldering technique is utilized to fixedly connect the handle with the probe-guide. In this regard, the handle itself is designed of a resilient or spring-like material, preferably spring quality stainless steel. In this way, it not only serves as a means of manipulating the combination probe-guide 12 and as a means for causing its finger-like segments to bear against the organ or tissue being biopsied, but also as a means for sensing the amount of force exerted by the probe-guide against the organ or tissue. More specifically, by designing a degree of resiliency into the handle itself, the operator is able to feel through the handle the amount of force he is exerting against the tissue at the finger-like segments for more accurately controlling the application of this force. This is to be contrasted with the use of a rigid handle which does not have the capability of transferring this sensitivity back to the operator's fingers since there is no give in the handle.

Turning now to FIGS. 3 and 4 in conjunction with FIG. 1, attention is directed to needle arrangement 16. This arrangement includes a specimen collecting needle 40 including a rearwardmost hub 42 adapted to receive a syringe 44 (FIG. 1). The needle is substantially longer than the combination probe-guide 12 as best seen in FIG. 1. In one actual embodiment, the shaft of needle 40 (excluding its hub) is 13 cm long and in another embodiment it is 15 cm long. This is to be contrasted with the length of the probe-guide 12 which is approximately 10 cm long in an actual working embodiment. As a result, when the needle shaft is inserted entirely through the probe-guide from the back end of the latter, a substantial front end section 46 of the needle shaft projects out beyond the front end of the probe-guide. In order to control the exact length of front end section 46 and hence the depth of penetration of the needle into the organ or tissue being biopsied, overall needle arrangement 16 includes an open-ended, tubular spacer 48. This spacer is designed to be positioned around the shaft of needle 40 at any desired point along its length and to fit sufficiently tight around the shaft so as to remain in place but not so tight as to cause damage to the shaft. In an actual working embodiment, spacer 48 is constructed of 18-8 stainless steel tubing and includes an inwardly directed, annular indent 50 which causes the interior wall of the spacer to grip the needle shaft. In actual operation, spacer 48 which has an outer diameter larger than the rearward entry to passageway 30 in the combination probe-guide 12 is disposed between the latter and hub 42. In this way, as the needle shaft is inserted through the probe-guide, spacer 48 engages the back end of the probe-guide to limit the maximum extent of section 46.

Referring to FIG. 3, overall needle arrangement 16 is also shown including a hollow stylet 52 including a stylet shaft 54 having a blunt front end 56 and a rearwardmost stylet hub 58. The stylet is slightly longer than needle 40 and serves two purposes. First, prior to using needle 40, the stylet serves as part of its packaging. More specifically, the shaft 54 of the stylet is initially disposed within the needle so that the front end section thereof extends beyond the pointed end of the needle shaft for protecting the latter which is extremely sharp and relatively delicate. However, the stylet itself also serves as a means to apply local anesthetic to the tissue being biopsied should this step be necessary. This is accomplished by removing the stylet from its associated needle and connecting it with an associated syringe filled with a local anesthetic. The stylet can then be directed into the area to be treated using the combination probe-guide and its associated handle.

Having described the various components making up overall assembly 10, attention is now directed to the way in which this assembly is used to collect a biopsy specimen. For the purpose of this discussion, it will be assumed that the tissue being biopsied is from a dog's kidney. However, it is to be understood that the assembly is suitable for obtaining biopsy specimens from other organs and tissue generally. In any event, it is first necessary to determine the position of the kidney (or other organ or tissue) to be biopsied. FIG. 5A illustrates diagrammatically the way a dog is positioned on a table and how assembly 10 is positioned for obtaining a biopsy specimen from its right kidney. FIG. 5B specifically illustrates the proper procedure for locating the incision site. FIG. 6A illustrates how the finger-like segments 26 of the probe-guide hold the right (or left) kidney and FIG. 6B provides further directions for locating the incision site. Finally, FIG. 7A shows how the needle 40 of assembly 10 penetrates the renal parencyma as the biopsy specimen is collected and FIG. 7B illustrates how a negative pressure is produced by pulling the plunger of syringe 44 in a rearward direction. To this end, a "woodpecker" like, that is, tapping motion with the needle severs a small specimen of renal tissue.

From all of the illustrations in FIGS. 5-7, it should be apparent that the entry incision need only be large enough to allow the probe-guide 12 to pass into the area of the kidney (or other tissue) and, hence, can be quite small. Before a specimen is actually collected, the probe-guide is inserted into position without the needle to apply a local anesthetic (if necessary or desirable) using the stylet 54 and to palpate the kidney. Through this latter procedure, the exact point on the kidney at which the specimen is to be collected is determined and the probe-guide is held in place with finger-like segments 26 resting against this point. The appropriate amount of force is exerted against the kidney by manipulation of handle 14. At the same time, needle 40 with spacer 48 appropriately positioned thereon is introduced into the probe-guide until front end section 46 rests on the kidney surface (capsule). A small amount of saline solution is infused to provide a seal, then negative pressure is applied by partial retraction of the syringe plunger. A woodpecker-like motion on the syringe 44 causes end section 46 to penetrate into the kidney to the desired depth. At this time, the woodpecker action of the biopsy needle and the negative pressure in the syringe 44 causes a tissue specimen to be aspirated into the needle shaft. In order to minimize the possibility of damage to this specimen, it is desirable to prevent the latter from being drawn into the syringe. To this end, a tissue stop 60 in the form of a length of wire is disposed within the shaft of the needle. Obviously, this wire stop must be sufficiently short to allow the specimen to be aspirated into the needle shaft but must be long enough to prevent the latter from passing all the way up into the syringe.

Having described the various components making up overall assembly 10 in a preferred embodiment and the method of using this assembly to obtain a biopsy specimen, attention is directed to an actual working embodiment. This embodiment includes a probe-guide 12 which is an integral unit constructed of 18-8 stainless steel and which is 10 cm long. The main body 18 of the probe-guide is cylindrical in cross-section and has an outer diameter of 2.41 mm (0.095") and an inner diameter of 1.8 mm (0.071"). Front end section 22 has a maximum outer diameter of 4.75 mm (0.187") as seen in FIG. 2B and each finger-like segment 24 is approximately 1.27 cm (0.500") long and 4.75 mm wide. The finger-like segment is approximately 2.54 mm in height with a rounded lower surface (when viewed from the side) extending into a narrow section equal in length to the elongated opening 28 which is 8.38 mm long. The handle 14 is constructed of a 2.5 cm wide band of spring quality stainless steel 0.035" or 0.889 mm in thickness which is folded on itself in the manner described above so as to provide an effective length (from bend 31 to section 38) of 7.2 cm. In this same actual embodiment, needle 40 is either 13 cm or 15 cm long (both have been used) and defines a 17 or 18 gauge bore. Using this assembly, it has been found that a relatively large specimen can be obtained, for example one which averages 1 mm wide by 6-15 mm in length.

While overall assembly 10 includes the various specific features just recited in a preferred embodiment, it is to be understood that the assembly is not specifically limited to these features. For example, while not preferred, the probe-guide itself could be grooved rather than tubular. This is best illustrated in FIGS. 8A and 8B which illustrate a probe-guide 12' having a front end section 22' similar to previously described front end section 22. However, the main body of probe-guide 12' includes an open channel 30' rather than previously described internal passageway 30. Moreover, rather than the specific handle 14 illustrated in FIG. 1, probe-guide 12' is manipulated by a handle arrangement 14' which is slightly different in shape, as seen in both FIGS. 8A and 8B. In fact, in the embodiment illustrated there, the handle arrangement 14' is an integrally formed part of the probe-guide.

In the embodiment illustrated in FIG. 9, a probe-guide 12" similar to probe-guide 12 is provided, that is, one utilizing a tubular body. However, in this embodiment, the handle which is generally indicated at 14" is relatively rigid (rather than resilient) and it is connected with probe-guide 12' in an adjustable manner. More specifically, a top set screw 14a" is provided along with a through-hole in the body of the handle for slidably receiving a probe-guide 12". The set screw cooperates with the through-hole to adjustably fix the position of the probe-guide within the latter.

Still another handle embodiment is illustrated in FIG. 10 in conjunction with a probe-guide 12''' which is substantially identical to previously described probe-guide 12. Moreover, the handle which is generally indicated at 14''' is quite similar to the resilient handle 14. However, the handle 14''' is interconnected with probe-guide 12''' by a connector 14a''' which serves to fixedly adjust the lengthwise position of probe-guide 12''' relative to handle arrangement 14''' in the same manner as handle 14".

What is claimed is:

1. An assembly especially suitable for performing biopsies on living organs or tissue, comprising: a straight, open-ended hollow tubular member serving as a combination probe and guide, said tubular member including a front end section having a substantially flat exterior surface substantially parallel with and on one side of the longitudinal axis of the tubular member for palpating the surface of the organ or tissue being biopsied to detect irregularities, spaced finger-like segments on the opposite side of said axis from said flat surface and extending outwardly away from said flat surface substantially perpendicular thereto for holding said organ or tissue in an immobile position while a biopsy specimen is collected and an opening into said tubular member on said opposite side and between said finger-like segments for gaining access through said tubular member to the organ or tissue held between said segments; handle means connected with said tubular member for holding the latter during performance of said biopsy; and means including a needle which is positionable through said tubular member for collecting said specimen.

2. An assembly according to claim 1 wherein said tubular member includes a continuous open groove extending its length from its front end segment between said spaced finger like segments to its back end said opening between said segments forming part of said groove.

3. An assembly according to claim 1 wherein said handle means includes a handle means of resilient material connected with said tubular member.

4. An assembly according to claim 3 wherein said handle is constructed of spring-like stainless steel sheet material connected with a back end section of said tubular member, said handle serving as a means for guiding said tubular member to and around said organ or tissue and as a means for causing the front end section of said tubular member to bear against said organ or tissue, the resiliency of said handle being such that the amount of force exerted by the front end section of said tubular member against said organ or tissue can be felt through the handle.

5. An assembly according to claim 4 wherein said handle is fixedly connected directly to the back end section of said tubular member at one of its own edges and is folded back on itself so as to provide two layers of said sheet material extending in a direction transverse to said tubular member.

6. An assembly according to claim 1 wherein said needle is longer than said tubular member and wherein said means including said needle also includes tubular spacer means positionable around said needle for limiting the extent to which said needle passes out the front end of said tubular member whereby to control the depth of penetration of the needle into said tissue.

7. An assembly according to claim 1 including means disposed within said needle for preventing a biopsy specimen collected by the front end of said needle from passing entirely through the needle.

8. An assembly according to claim 1 including a second open-ended hollow tubular member having a blunted front end, said second member serving to protect said needle and as a stylet for directing local anesthetic into the area of said tissue, said second member being sufficiently small in cross-section to pass through both said first tubular member and said needle.

* * * * *